(12) United States Patent
Schnell

(10) Patent No.: US 10,034,992 B2
(45) Date of Patent: Jul. 31, 2018

(54) SPEAKING VALVE

(71) Applicant: TRACOE medical GmbH, Nieder-Olm (DE)

(72) Inventor: Ralf Schnell, Seligenstadt (DE)

(73) Assignee: TRACOE MEDICAL GMBH, Nieder-olm (DE)

( * ) Notice: Subject to any disclaimer, the term of this patent is extended or adjusted under 35 U.S.C. 154(b) by 387 days.

(21) Appl. No.: 14/426,710

(22) PCT Filed: Oct. 8, 2013

(86) PCT No.: PCT/EP2013/070921
§ 371 (c)(1),
(2) Date: Mar. 6, 2015

(87) PCT Pub. No.: WO2014/060242
PCT Pub. Date: Apr. 24, 2014

(65) Prior Publication Data
US 2015/0238718 A1    Aug. 27, 2015

(30) Foreign Application Priority Data
Oct. 17, 2012 (DE) .......................... 10 2012 109 916

(51) Int. Cl.
*A61M 16/04* (2006.01)
*A61M 16/08* (2006.01)
(Continued)

(52) U.S. Cl.
CPC ........... *A61M 16/0468* (2013.01); *A61F 2/20* (2013.01); *A61M 16/0816* (2013.01);
(Continued)

(58) Field of Classification Search
CPC . A61F 2/20; A61M 16/0427; A61M 16/0468; A61M 16/047; A61M 16/0488;
(Continued)

(56) References Cited

U.S. PATENT DOCUMENTS 4,759,356 A * 7/1988 Muir ................. A61M 16/0468
128/207.16
4,763,645 A * 8/1988 Kapp ................. A61M 16/047
128/205.29
(Continued)

FOREIGN PATENT DOCUMENTS

DE    202005006605 U1    4/2005
DE    202010014245 U1    3/2011
(Continued)

OTHER PUBLICATIONS

Nora Linder, International Preliminary Report on Patentability, International Bureau of WIPO, dated Apr. 21, 2015.
(Continued)

*Primary Examiner* — Annette Dixon
(74) *Attorney, Agent, or Firm* — Paul & Paul

(57) ABSTRACT

A speaking valve for fitment on to a tracheostomy cannula includes a valve unit and an attachment unit. The attachment unit has a tubular housing having a first and a second end and a longitudinal axis extending from the first to the second end. The first end of the attachment unit can be connected to a connector on the tracheostomy cannula and the valve unit is arranged at the second end of the attachment unit. The valve unit and the attachment unit are connected together movably. The valve unit is designed that in a first position it closes the housing of the attachment unit air-tightly with respect to a flow direction, and in at least one second position it permits a flow of air into the housing and out of the housing.

22 Claims, 8 Drawing Sheets

(51) Int. Cl.
*A61F 2/20* (2006.01)
*A61M 16/10* (2006.01)
*A61M 16/20* (2006.01)

(52) U.S. Cl.
CPC ....... *A61M 16/105* (2013.01); *A61M 16/1045* (2013.01); *A61M 16/208* (2013.01); *A61M 2205/581* (2013.01); *A61M 2205/7536* (2013.01); *F04C 2270/041* (2013.01)

(58) Field of Classification Search
CPC ............ A61M 16/1045; A61M 16/107; A61M 16/208; Y10S 128/26; Y10S 128/911; Y10S 128/912; Y10T 137/784
USPC ............ 128/201.13, 207.14, 207.15, 207.16, 128/207.18, 911, 912; 623/9
See application file for complete search history.

(56) References Cited

U.S. PATENT DOCUMENTS

| | | | | |
|---|---|---|---|---|
| 5,606,966 A | * | 3/1997 | Smith | A61M 16/0465 128/200.26 |
| 5,738,095 A | * | 4/1998 | Persson | A61F 2/20 128/201.13 |
| 6,386,200 B1 | | 5/2002 | Zowtiak | |
| 6,802,316 B1 | * | 10/2004 | Fulgham | A61M 16/0468 128/207.14 |
| 2004/0123868 A1 | * | 7/2004 | Rutter | A61M 16/0468 128/207.14 |
| 2012/0097170 A1 | * | 4/2012 | Dawson | A61M 16/0468 128/207.16 |

FOREIGN PATENT DOCUMENTS

| | | |
|---|---|---|
| DE | 202012001825 U1 | 2/2012 |
| EP | 2236165 A1 | 10/2010 |
| GB | 2313317 A | 11/1997 |
| WO | 2011062533 A1 | 5/2011 |

OTHER PUBLICATIONS

Mourad Azaizia, European Patent Office, International Search Report, dated Dec. 13, 2013.

Hans Hockenreiner, German Patent and Trademark Office, German Search Report, dated Apr. 16, 2013.

* cited by examiner

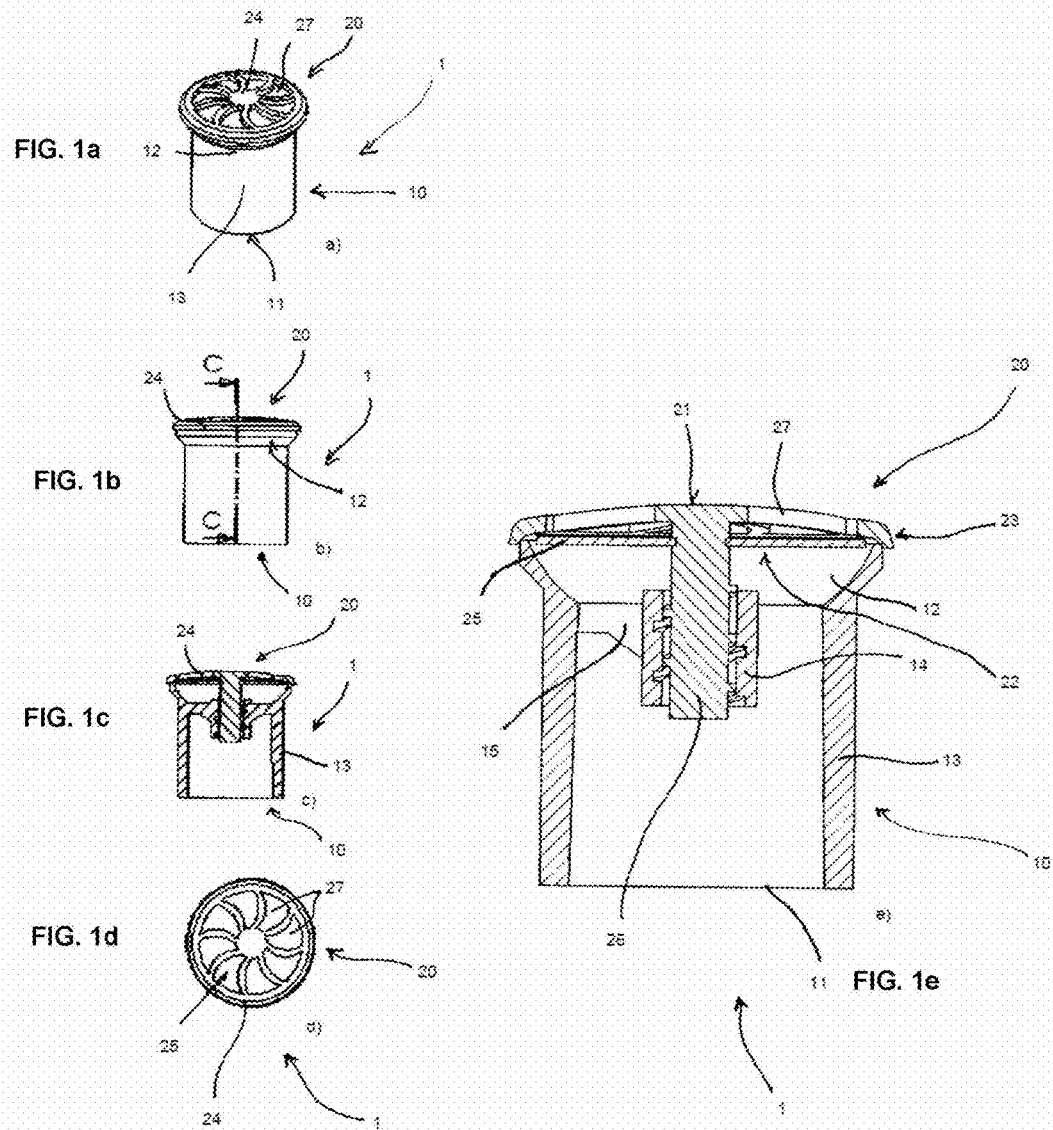

SPEAKING VALVE

CROSS-REFERENCE TO RELATED APPLICATION

This is a national stage 371 application of International Application No. PCT/EP2013/070921, filed Oct. 8, 2013.

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable

STATEMENT REGARDING PRIOR DISCLOSURES BY THE INVENTOR OR A JOINT INVENTOR

Not applicable

BACKGROUND OF THE INVENTION

Field of the Invention

The invention concerns a speaking valve for fitment on to a tracheostomy cannula, which includes a valve unit and an attachment unit, wherein the attachment unit has a tubular housing having a first and a second end and a longitudinal axis extending from the first to the second end, wherein the first end of the attachment unit can be connected to a connector on the tracheostomy cannula and the valve unit is arranged at the second end of the attachment unit and wherein the valve unit and the attachment unit are connected together movably as well as a tracheostomy cannula equipped with such a speaking valve.

Description of Related Art Including Information Disclosed Under 37 C.F.R. 1.97 and 1.98

In the case of patients whose breathing is facilitated through a tracheostoma into which a tracheostomy cannula is introduced air enters downstream of the larynx into the lower airways and also issues again. Discharge of the air through the tracheostoma or the tracheostomy cannula can be prevented by simply blocking the cannula tube for example with a finger, whereby the air upon exhalation is then passed by way of the natural airways, that is to say the larynx and the mouth or the nose, and the vocal chords can be caused to vibrate for producing sound.

To make it easier for patients with a tracheostomy to speak, valves are known which are provided for fitment to a tracheostomy cannula and which are so designed that they open upon inhalation so that air can flow in through the tracheostomy cannula and they close upon exhalation so that the air is passed by way of the natural airways without having to manually close the tracheostomy cannula. When using such valves not only is speaking made easier but in addition a therapeutic purpose is also achieved by passing exhaled air by way of the natural airways, namely inter alia training the swallowing reflexes.

The use of a speaking valve however can become very strenuous and uncomfortable for a patient after a prolonged time. That can be due on the one hand to the fact that the force that the patient has to apply for exhalation by way of the natural airways can be tiring. That increased application of force is caused inter alia by the fact that the muscles necessary for independent respiration weaken and are less trained in the case of patients with a tracheostomy after some time. On the other hand the valve function can have the result that more air can be inhaled than exhaled, the phenomenon known as 'air trapping'. That results in an increased pressure in the lower airways, that is unpleasant to the patient. Inhalation can also be made difficult by virtue of the fitment of a speaking valve.

To obviate that problem speaking valves are known which can be opened to permit exhalation through the tracheostomy cannula when speech and thus exhalation by way of the natural airways is not wanted or is not required. In other known speaking valves the problem is solved by lateral windows being provided between the tracheostomy cannula and the actual valve, which windows can be opened and closed by displacement of an element with slots, that is arranged displaceably relative thereto.

No such devices are provided in most speaking valves so that, upon the occurrence of the above-indicated problems, the speaking valve has to be completely removed from the tracheostomy cannula.

BRIEF SUMMARY OF THE INVENTION

With the background of that state of the art in mind therefore the object of the invention is to provide an alternative to known speaking valves, in which in spite of using a speaking valve it is possible, if this is desired, to exhale through the tracheostoma by bypassing the valve function.

According to the invention that object is attained by a speaking valve of the kind set forth in the opening part of this specification in that
  the valve unit is so designed and arranged that
  in a first position it closes the housing of the attachment unit air-tightly with respect to a flow direction, and
  in at least one second position it permits a flow of air into the housing and out of the housing,
  wherein the valve unit can be transferred from the first into the at least one second position by a movement parallel to the direction of the longitudinal axis of the tubular housing.

In that respect the first position corresponds to the known mode of operation of a speaking valve in which only inhalation is possible through the valve while exhalation is prevented by a valve element and the respiratory air therefore has to escape by way of the natural airways. The second position in contrast defines a speaking valve which is open in both directions.

That configuration makes it possible to provide a speaking valve involving a small space, in which the valve function can be bypassed easily and without painful manipulation at the tracheostomy cannula. In addition, by providing a plurality of 'second' positions for the valve portion an opening between the valve unit and the attachment unit can be varied in such a way that different flow resistances are afforded for exhalation through the tracheostoma. In that way it is possible to set positions in which a part of the inhaled air is discharged through the upper airways and a part is discharged through the attachment unit of the speaking valve.

For regular function of a speaking valve of such a configuration the valve unit is provided and designed so that air can pass through the speaking valve into the tracheostomy cannula and ultimately into the lungs, even if the valve unit is in the first position, wherein, in that position in which the valve unit air-tightly bears against the tubular housing of the attachment unit, a through-flow of air in the opposite direction (that is to say upon exhalation) is prevented by the valve action of the valve unit. The function of the valve unit therefore involves allowing a flow of air from the outside through the valve unit in the direction of the attachment unit and preventing a flow of air in the opposite direction. Known valve devices can be used in the valve unit or as the valve unit, for implementing that function.

Preferably in the first position an annular surface extending perpendicularly to the longitudinal axis or conically at the second end of the tubular housing and an annular end face of the side of the valve unit, that faces towards the attachment unit, bear air-tightly against each other.

In an embodiment the valve unit is so constructed that in the first position it completely covers the circular opening at the second end of the tubular housing and possibly projects radially beyond the edge of that opening.

The term tubular housing denotes a housing which is substantially in the form of a hollow cylinder, wherein its inside wall and/or outside wall can converge conically, in particular in the direction of the second end. The tubular housing of the attachment unit is open at both ends. In certain embodiments, at its outside and/or inside, the tubular housing has portion-wise enlargements or narrowings. A portion-wise enlargement in the proximity of the second end provides for example space for the introduction of a filter or other items or space for a movement of a component part of the valve unit upon opening of the valve for an inflow of air in the direction of the attachment unit or into the attachment unit.

The 'longitudinal axis of the tubular housing' as used herein denotes the axis extending centrally from the first to the second end of the tubular housing and in relation to which the tubular housing has a rotational symmetry, wherein the term tubular housing also embraces housings whose cross-section is substantially polygonal, for example quadrangular, pentagonal, hexagonal or octagonal.

In an embodiment the extent of the tubular housing or the attachment unit on the outside is between 16 and 26 mm.

In an embodiment the valve unit can be steplessly converted from the first into a second position by a movement parallel to the direction of the longitudinal axis of the tubular housing and it is possible to set between the first and second position any desired number of positions in which the valve unit is spaced from the housing of the attachment unit. That occurs for example by a thread engagement between the attachment unit and the valve unit.

In that respect in an embodiment the attachment unit has a male thread and the valve unit (which also has a tube portion) has a female thread matching same or vice-versa.

In an embodiment the valve unit is movable between the first and second positions and it is possible to set various defined second positions in which the valve unit permits a passage of air to and from the inside of the attachment unit with respectively different flow cross-sections or flow resistances.

In an embodiment the valve unit is in the form of a valve cap having a cylindrical cap casing portion and a disk-shaped valve cover.

Desirably the cap casing portion has at least one opening which in the first position is covered by a wall of the attachment unit, that bears against the surroundings of the opening, and which in the second position is opened by the wall of the attachment unit.

For example the attachment unit substantially comprises a tubular housing with attachment or connecting elements at the valve-side end and the opposite end. The valve unit can be for example in the form of a cap having a cylindrical casing portion, which is fitted on to an end of the tubular attachment unit, wherein the inside diameter of the cap casing portion substantially corresponds to the outside diameter of the attachment unit and wherein those two elements can also be connected together by thread engagement.

The cover of the cap forms a valve seat having a plurality of apertures which are covered from the inside by a valve diaphragm. In addition the cylindrical cap casing portion in the proximity of the cover may also have openings or apertures which are covered in the first position by the wall of the tubular attachment unit, wherein preferably the edge at the valve-side end of the attachment element comes into sealing contact with the inside surface of the cover or the valve unit. For that purpose for example the transition between the cylindrical casing surface and the cover at the inside of the valve unit may also be conical, which ensures good sealing engagement. Alternatively however an outer cylindrical end portion of the attachment unit can also be guided in fitting and sealing relationship in the cap casing portion which has at least one opening, so that the wall of the attachment unit in the first position covers the opening or orifice in the cap casing portion and opens the opening in a position of being displaced relative to the cap or the cylindrical portion of the valve unit so that air can flow in through the opening and into the end orifice of the attachment element.

For that purpose it is sufficient for example if the valve unit is displaceable relative to the attachment unit by an amount of between 2 and 5, preferably between 3 and 4 mm, wherein the first position is defined by a front end of the attachment element butting against the cover of the cap-shaped valve unit or against a conical transition on the inside between the cylindrical casing portion and the cover of the valve unit while the second position is characterised by a spacing of the edge of the attachment unit from the valve cover and that spacing is between 2 and 5, preferably less than 4 and in particular about 3 mm.

In an embodiment the valve unit can also be separated completely from the attachment unit independently of the first and at least one second position relative to the attachment unit. That has the advantage that the individual elements of the speaking valve can be more easily cleaned, disinfected and (for example in regard to a moisture/heat storage means or filter) replaced.

In an embodiment the attachment unit has at least one first connecting element and the valve unit has at least one second connecting element, wherein the at least one first and at least one second connecting elements are so designed that they respectively form an opening and a projection corresponding thereto, and the attachment unit and the valve unit are movably connected by way of the interengaging first and second connecting elements. Such connecting elements are advantageous in regard to the configuration of the connecting elements of the attachment unit and the valve unit respectively as they allow a movement between a first position and at least one second position.

In the above-described variant the connecting elements are formed on the one hand by the tubular housing of the attachment unit and on the other hand by the cylinder casing portion of a cap-shaped valve element. In a further embodiment the connecting elements are provided centrally and separately from the outer cylindrical housing of the attachment unit or a cap casing portion or outer cylindrical junction portion of a valve element. That variant is described hereinafter.

In an embodiment the at least one first connecting element is provided in the region of the wall of the tubular housing and the at least one second connecting element is provided at a corresponding location in the region of an edge of the valve unit on the side of the valve unit, facing towards the attachment unit.

In an embodiment the at least one first connecting element is arranged in the region of the hollow space of the tubular housing and the at least one second connecting element is arranged on the side of the valve unit, facing towards the attachment unit, spaced from the edge of the valve unit, or, in other words, it is arranged in corresponding relationship with the arrangement of the first connecting element on the valve unit. In such embodiments the first connecting element is preferably connected to the inside wall of the tubular housing by way of legs.

In an embodiment the at least one first connecting element is formed in one piece with the attachment unit and/or the at least one second connecting element is formed in one piece with the valve cover. Such a one-piece configuration enhances the stability of the respective units of the speaking valve.

In an embodiment either the attachment unit or the valve unit has at least one projection and the respective other unit has at least one receiving opening corresponding thereto, wherein the attachment unit and the valve unit are connected together movably and preferably releasably by way of the engagement of the projection with the receiving opening. As already mentioned projection and receiving opening can be formed by interengaging thread flights, but this can also involve a plurality of mutually spaced latching elements.

Connecting elements of such a configuration permit stepless movement or a stepped movement at defined spacings of the sealing surface of the valve unit from or to the second end of the housing of the attachment unit. Such connections can also be easily operated by the patient who has had the tracheostomy himself and who has a tracheostomy cannula with such a speaking valve and does not require any visual contact in operation.

In an embodiment the at least one first and at least one second connecting element come into engagement with each other in completely releasable relationship. In that way, irrespective of the setting of the first and a second position, it is possible for the valve unit to be completely separated from the attachment unit, so they can be more easily cleaned.

In an embodiment the valve unit substantially comprises an apertured cover, the inside of which is covered by a valve diaphragm.

In an embodiment the valve cover also has a central cylindrical junction portion serving as a connecting element with the attachment unit. In this case also the attachment unit is again substantially in the form of a cylindrical tube, on one end of which or on the end edge of which the valve cover is seated (in the first position) with its outer edge. The tubular attachment element also has a smaller cylindrical inner tube connected to the inside wall of the tubular housing of the attachment element by way of legs. The central cylindrical junction portion of the valve cover and the inner tube of the attachment element, that is held by way of legs, form connecting elements, by way of which the valve unit and the attachment element are connected together, wherein those connecting elements can again be provided with latching elements or also with female or male threads so that, by virtue of a relative rotary movement, axial displacement is possible and thus the valve cover can be caused to axially lift off the edge of the attachment element so that an opening is cleared between the valve cover and the edge of the attachment element.

It will be appreciated that, in a kinematic reversal, the valve element could have a central tubular attachment portion while a pin held by way of legs could be provided in the interior of the tubular attachment element, the pin engaging into the tubular attachment portion of the valve cover.

In an embodiment therefore the first or the second connecting element is in the form of a cylinder and the respective other one is in the form of a hollow cylinder, the longitudinal axes of which extend on the longitudinal axis of the tubular housing and which come into engagement with each other with a screwing or latching connection or a combination thereof, in which case the cylinder is or becomes introduced into the hollow cylinder.

The term 'cylinder as is used here in this context denotes a cylindrical body of a substantially circular cross-section or a hollow cylinder of a substantially annular cross-section.

In an embodiment arranged in the proximity of the second end in the flow cross-section of the tubular housing of the attachment unit is an air-permeable, moisture and heat-storing material, for example in the form of a disk, which here is also referred to as the 'filter element'. Such a material is preferably elastically or plastically deformable and, for example if it is in the form of a circular disk, it can be received in a peripherally extending groove or recess in the inside surface of the tubular attachment unit. It will be appreciated that the diameter of the circular disk is then adapted to the inside diameter of the corresponding groove or recess. A corresponding disk is for example between 15 and 25 mm in diameter and is of a thickness of between 1 and 8 mm, preferably about 3 mm. In that case the filter element can also partially project beyond the second end of the tubular housing in the direction of the valve unit or it terminates with the second end of the tubular housing or it is so arranged in the region of the second end of the tubular housing that it is disposed at a spacing relative to the second end of the tubular housing. The spacing is preferably not more than 3 mm but it should still be sufficient so that the diaphragm of the valve, that lies thereover, has sufficient clearance for movement to allow respiratory air to flow in. The filter material is for example a sponge-like material which can preferably comprise an open-pore plastic or also a special paper. In an embodiment the material is hydrophilic or hygroscopic, for example being coated with $CaCl_2$, to improve the capacity for moisture storage.

For an embodiment of the speaking valve in which the first and second connecting elements extend in the center of the tubular housing the disk-shaped filter element preferably has a central aperture and is arranged around the first and/or second connecting element.

In an embodiment the valve unit has a disk-shaped valve cover and a valve diaphragm, wherein the outwardly facing side and the peripheral surface of the valve unit are formed by the valve cover and, at a side of the valve cover, that faces towards the attachment unit, a valve diaphragm is fixed to the valve cover, the valve cover forming a valve seat and being apertured portion-wise in a region in which the valve diaphragm bears thereagainst. Such an arrangement ensures that, when the valve unit is disposed in the first position relative to the attachment unit, air can be passed through the openings/apertures in the valve cover past the valve diaphragm into the interior of the tubular housing and as a result ultimately into the tracheostomy cannula and finally into the lungs of the patient. Conversely a flow of air in the opposite direction provides that the valve diaphragm is pressed against the valve seat and covers the portion-wise apertures. That prevents air from flowing out through the speaking valve. In an embodiment the valve seat is in the form of an annular web which extends around the apertures in the valve cover and which forms the valve seat and which at the same time causes a certain prestressing of the valve diaphragm into the closed position, which for example is fixed in the form of a flat disk of elastic material centrally to the inside surface of the valve cover.

A 'disk-shaped valve cover' as used herein denotes an element which is substantially in the form of a flat cylinder, the thickness or height of which is less than its radius. This can involve a circular cylinder but also a cylinder with a polygonal base surface like a quadrangular, hexagonal or octagonal surface. In addition this term as is used herein also includes a configuration wherein the disk-shaped valve cover can have a curvature. In an embodiment the valve cover has a concave curvature on the side facing towards the attachment unit and possibly a convex curvature on the outwardly facing side. The disk-shaped valve cover can further have thickened portions, grooves or other depressions or peripherally extending reductions in thickness and can be for example shaped substantially like a frisbee.

Preferably the valve diaphragm does not extend to the outermost edge of the side of the valve cover, that faces towards the attachment unit, wherein in the first position of the valve unit the edge of the side of the valve cover, that faces towards the attachment unit, bears air-tightly against the second end of the tubular housing.

In an embodiment the valve diaphragm is of a material thickness of between 0.1 mm and 1 mm, preferably between 0.2 mm and 0.5 mm. In an embodiment the diaphragm is made from silicone, EVA, SEBS or another thermoplastic material.

In an embodiment the valve diaphragm has edge regions and a central region and is so fitted with the central region to the valve cover that the edge regions can lift off the valve cover in the direction of the attachment unit. The above-described valve action is ensured by such a configuration. In an embodiment in that case the valve diaphragm bears with its edge region in a prestressed condition against the side of the valve cover, that faces towards the attachment unit. Such a prestressing ensures that the valve diaphragm bears snugly against the region of the valve cover, that has apertures, wherein for example a pressure difference of about 5 mbar is needed to open the valve.

In an embodiment the second connecting element which is connected to the valve cover simultaneously provides for fixing the diaphragm to the valve cover.

In an embodiment the connecting elements of the valve unit and the attachment unit are arranged on the longitudinal axis of the housing and the diaphragm is fixed to the valve cover in a region extending around the longitudinal axis, wherein both the fixing of the diaphragm and also the connecting elements are in the form of hollow cylinders and the valve cover has a central opening, a structure in the form of a hollow cylinder with open ends being formed, which extends through the valve cover and the entire valve unit and ends in the attachment unit. Such a configuration provides within the valve cover an orifice for the connection of an oxygen tube which in normal use of the speaking valve is closed by a closure element like for example a plug.

In an embodiment the valve cover comprises an elastic material and in the first position of the valve unit bears with a prestressing air-tightly against the second end of the housing, in which case the valve cover is pressed partially outwardly upon an increased pressure in the speaking valve so that its edge no longer bears against the second end of the tubular housing. The prestressing can for example be so selected that a pressure difference of between about 30 and 50 mbar is required to lift the cover (valve seat) off its engagement with the end of the tubular housing of the attachment unit. In such a design configuration the valve cover can function as a kind of 'pressure-relief valve' which, in the event of a strong internal pressure in the speaking valve, pivots away outwardly in opposite relationship to the elastic prestressings and thereby permits air to escape.

The expression 'in the speaking valve' denotes the lumen of the housing, which in the first position of the valve unit is delimited at the second end by the valve unit and at the first end transitions into the lumen of the tracheostomy cannula.

In an embodiment the peripheral surface of the valve unit is provided with a grooving, roughening and/or a projection or depression in the peripheral surface. Such roughenings or groovings or projections and depressions make it easier to grip the valve unit or the valve cover at the peripheral surface and thus facilitate handling of the speaking valve when moving the valve unit from the first position into the at least one second position or vice-versa. In addition a projection or a depression provided at a single location in the peripheral surface, in particular when the arrangement involves a screw connection between valve cover and housing of the attachment unit, provides an indicator which can be detected by feel for the open condition of the speaking valve. In certain embodiments a projection disposed at a location may be in the form of an eye, lug, hemisphere or the like.

In an embodiment the valve unit has latching elements which preferably audibly come into latching engagement. In addition there can be provided one or more markings which are visible or which can be felt from the exterior, by means of which it is possible to detect the position of the speaking valve.

In an embodiment the housing of the attachment unit and the peripheral surface of the valve unit together are of a conically outwardly tapering form. With suitable matching to common dimensions of female connections of respiratory tubes such a form can provide an oxygen connection, by means of which the patient can be supplied with oxygen. When the oxygen connection is fitted the oxygen can escape through the upper airways. In an embodiment the taper ratio of the outwardly conically tapering shape is 1:40, an outer diameter of the housing of the attachment unit being 22 mm at a location. Preferably the location is substantially in the center between the first and the second ends, in which respect deviations from the center of up to +/−3 mm are possible.

In an embodiment the first end of the attachment unit can be fitted in frictionally locking relationship on to the connector on the tracheostomy cannula. For the attachment of oxygen connections or further accessories tracheostomy cannulae are provided with a connector which is of dimensions permitting such fitment. Preferably the inside wall of the housing of the attachment unit is adapted to such dimensions.

The object set out in the opening part of this specification is also attained by a tracheostomy cannula having a speaking valve in accordance with the above-described variants.

Further advantages, features and possible uses of the present invention will be apparent from the description hereinafter of preferred embodiments and the related Figures in which:

BRIEF DESCRIPTION OF THE SEVERAL VIEWS OF THE DRAWING(S)

FIG. 1a is a perspective view of a first embodiment of a speaking valve according to the invention in a first position of the valve unit.

FIG. 1b is an elevational view of a first embodiment of a speaking valve according to the invention in the first position of the valve unit.

FIG. 1c is a sectional elevational view taken along the line C-C of FIG. 1b of a first embodiment of a speaking valve according to the invention in the first position of the valve unit.

FIG. 1d is a top plan view of a first embodiment of a speaking valve according to the invention in the first position of the valve unit.

FIG. 1e is an enlarged sectional view taken along the line C-C of FIG. 1b of a first embodiment of a speaking valve according to the invention in the first position of the valve unit.

Figure 4:
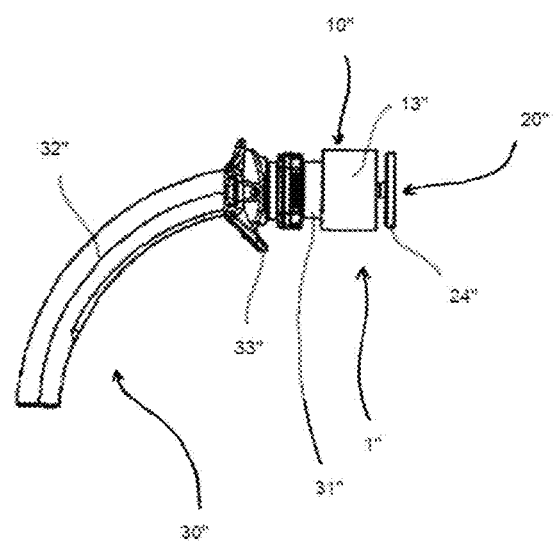
Figure 5:
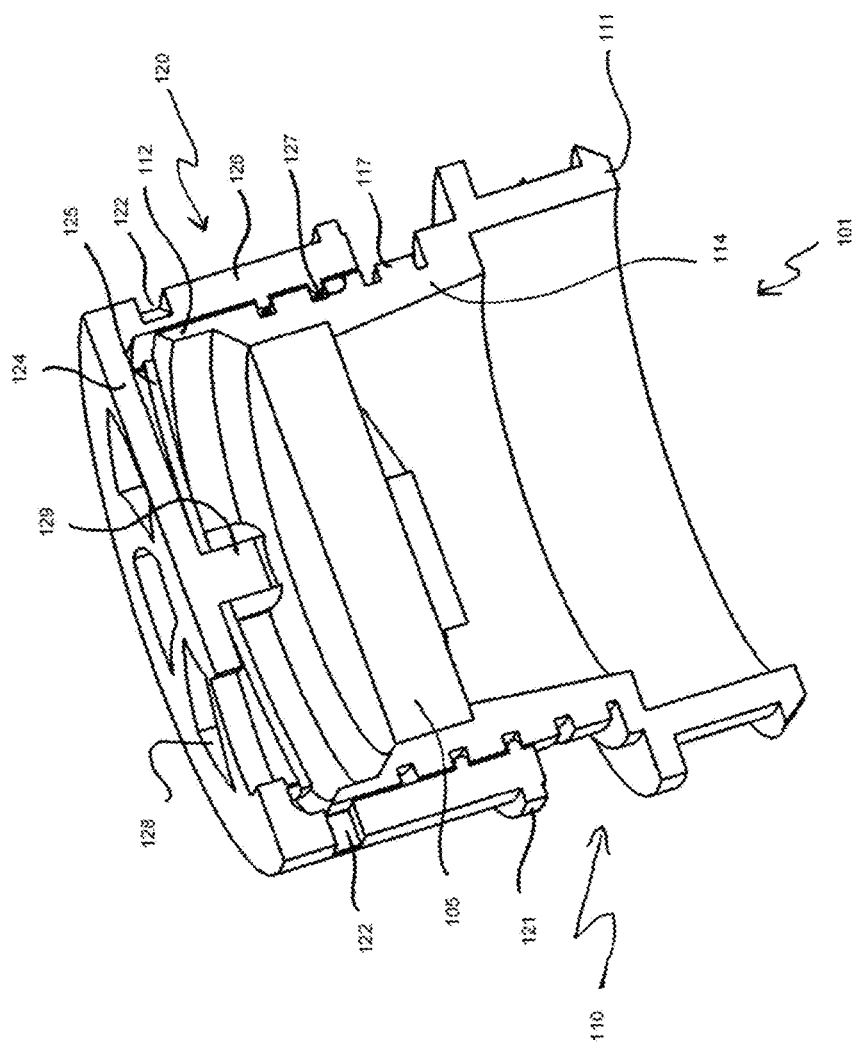
Figure 6:
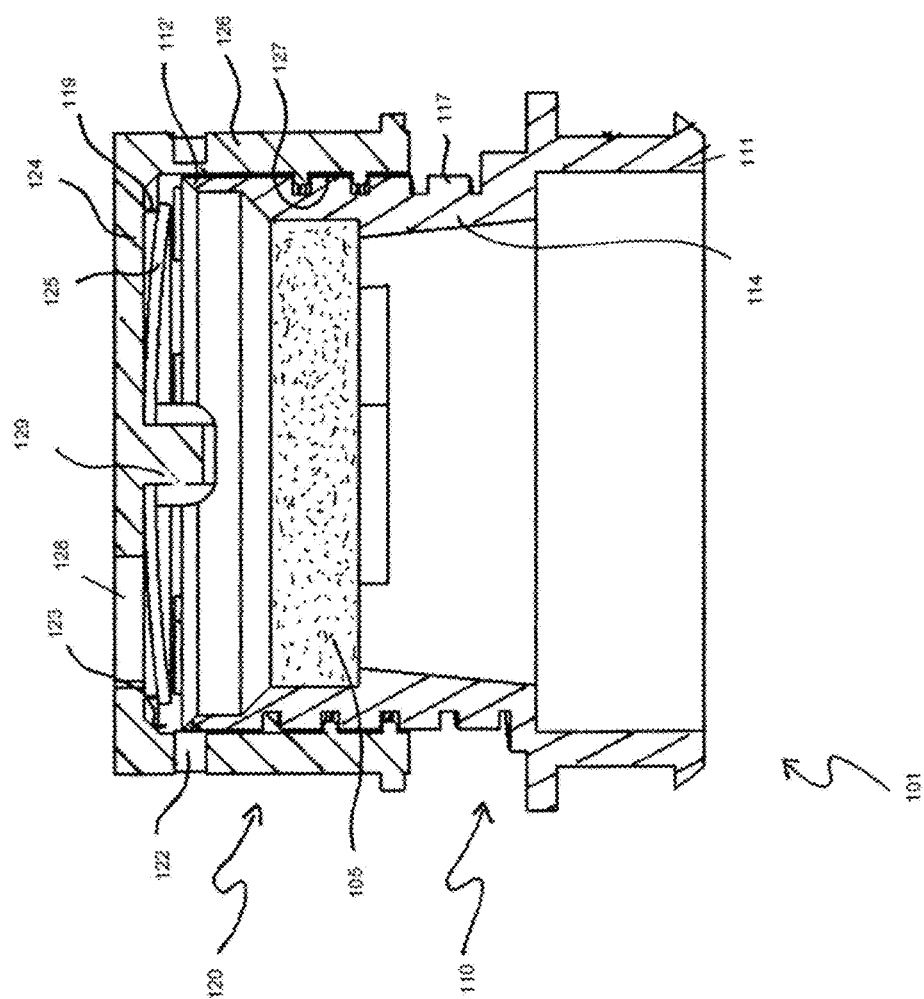
Figure 7:
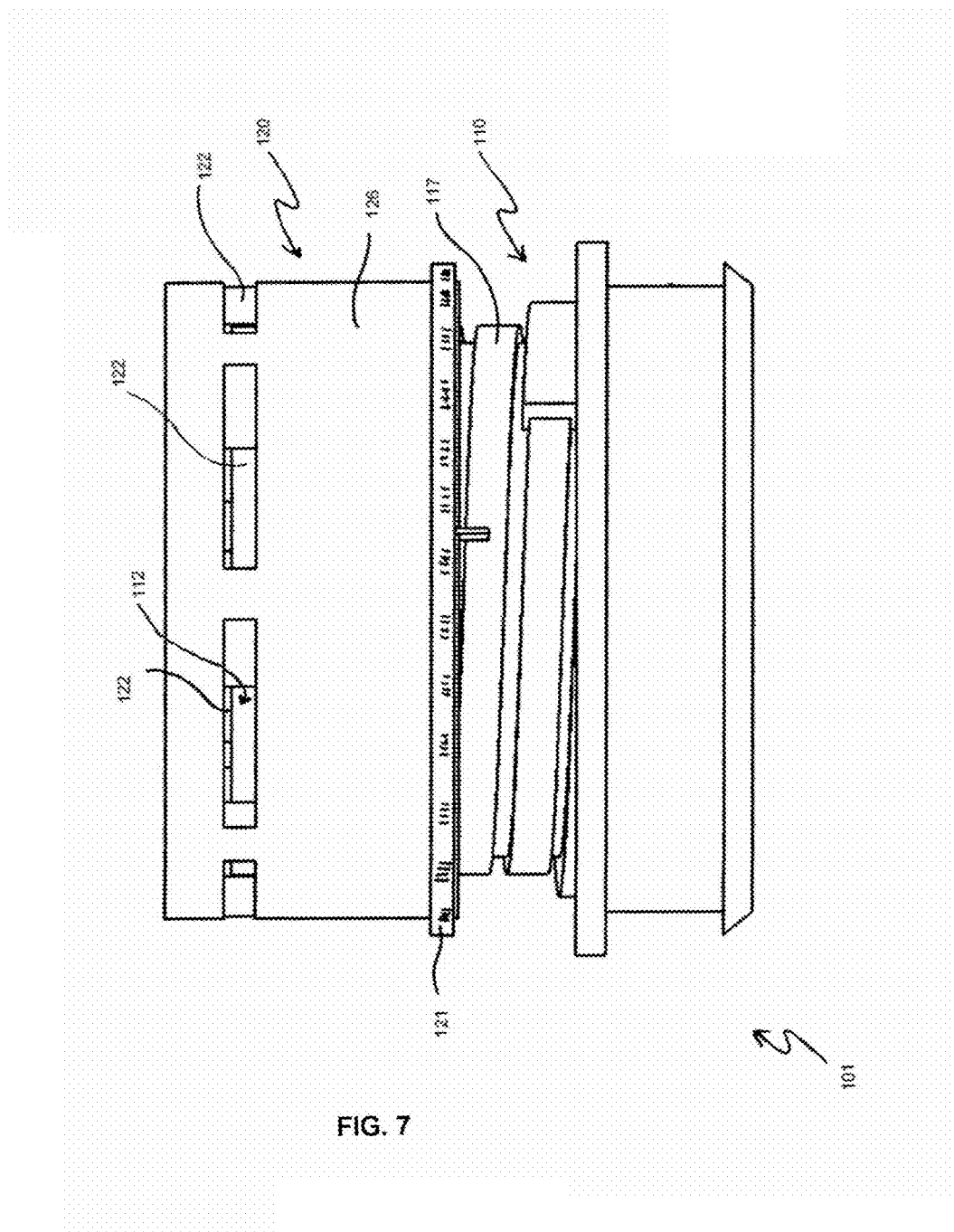
Figure 8:
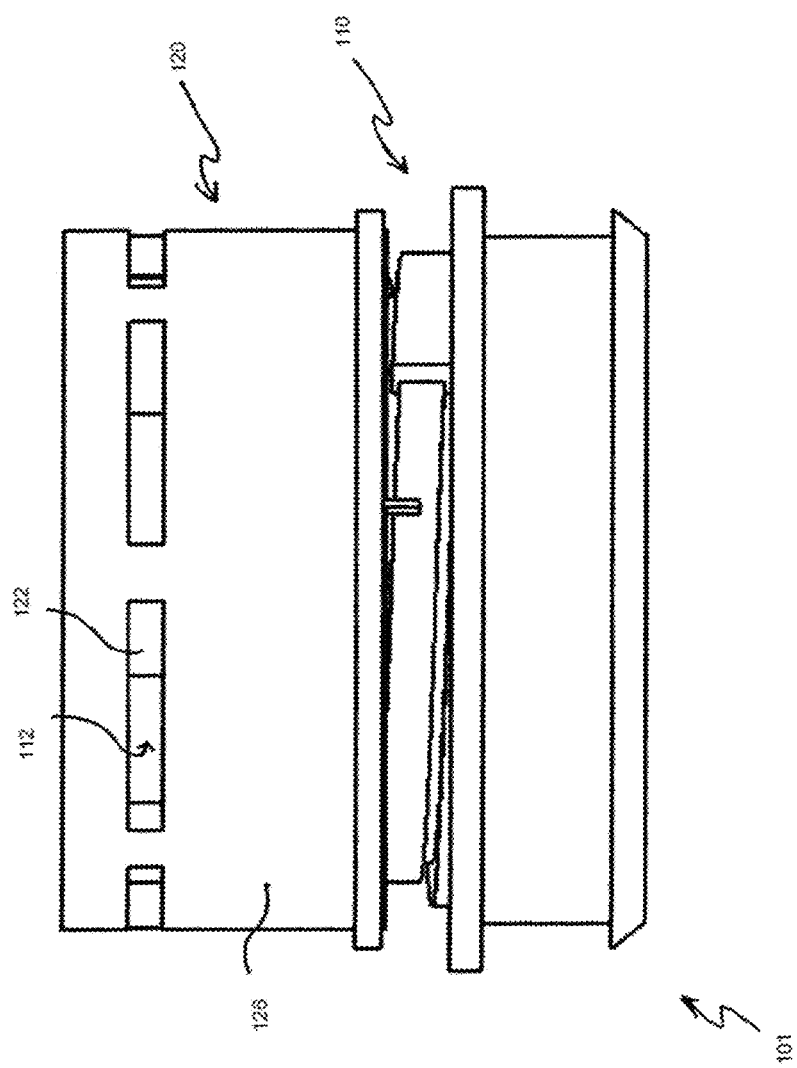

FIG. 4 shows a further embodiment of a speaking valve according to the invention which is fitted on to a tracheostomy cannula, FIG. 5 is a partly sectional perspective view of a further embodiment, FIG. 6 shows a section containing the axis of the embodiment of FIG. 5, FIG. 7 shows a side view of the speaking valve of FIG. 5 in a partially opened condition, and FIG. 8 shows a side view of the speaking valve of FIG. 5 in a substantially closed condition.

DETAILED DESCRIPTION

FIG. 1 shows a speaking valve according to the invention in the first position of the valve unit. In that case FIG. 1a is a perspective view of such a speaking valve, FIG. 1b is a side view on to the speaking valve, FIG. 1c is a sectional view along line C-C, FIG. 1d is a plan view on to the outwardly facing side of the valve cover and FIG. 1e shows an enlarged view of FIG. 1c.

In this embodiment of the speaking valve 1 the valve unit 20 has a valve cover 24 and a valve diaphragm 25, wherein the valve diaphragm is connected in a central region to the valve cover and does not cover its edge of the side 22 facing towards the attachment unit 10. In the first position the valve cover 24 of the valve unit 20 bears sealingly against the second end 12 of the tubular housing 13. In this embodiment the second end 12 of the tubular housing 13 has a conically enlarging end portion, against which the valve cover 24 bears with the edge of its side 22 facing towards the attachment unit 10, wherein the edge of the valve cover 24 is stepped and narrows in the region of the contact surface against the second end of the tubular housing 13 of the attachment unit 10.

The tubular housing 13 and the valve cover 24 each have a respective connecting element 14 and 26 respectively which are substantially cylindrical and are arranged on the longitudinal axis of the tubular housing. The first connecting element 14 of the tubular housing is fixed to the inside wall of the tubular housing 13 with legs 15. Overall the first connecting element and the second connecting element provide a screw connection. The second connecting element 26 on the valve cover at the same time fixes the valve diaphragm 25 at the side of the valve cover 24, that faces towards the attachment unit. The valve cover has apertures 27 which, if there is not a reduced pressure within the tubular housing of the attachment portion in comparison with the exterior, are covered by the diaphragm 25 which bears against the valve cover (with prestressing?).

Figures 2A, 2B, 2C:
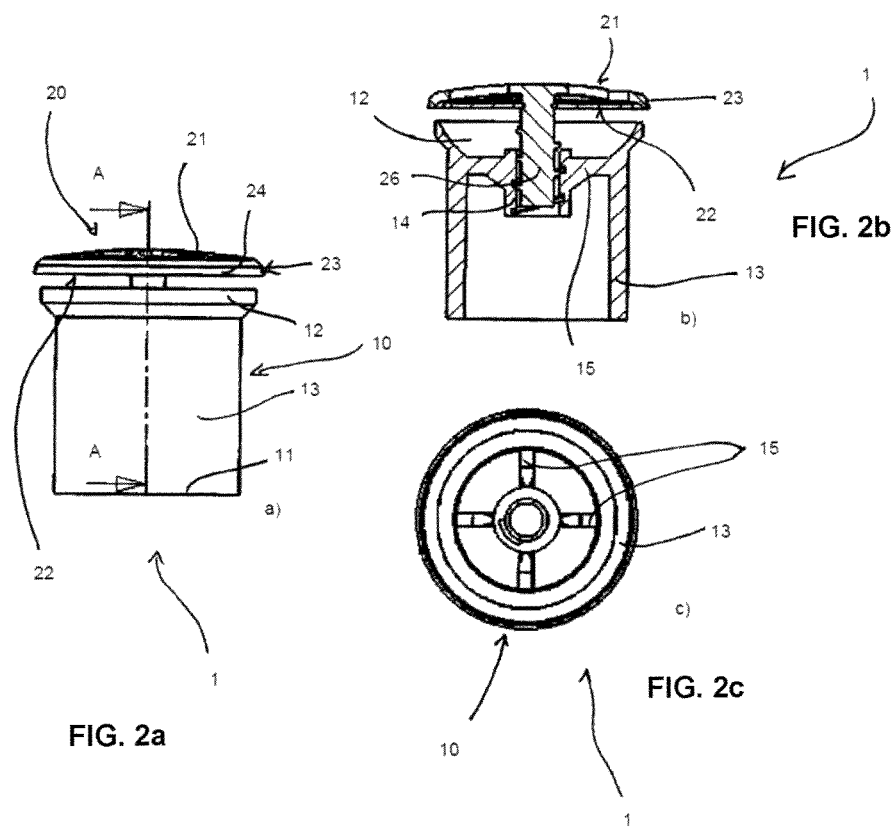
FIG. 2a is an elevational view of a first embodiment of a speaking valve according to the invention in a second position of the valve unit.
FIG. 2b is a sectional view taken along the line A-A of FIG. 2a of a first embodiment of a speaking valve according to the invention in the second position of the valve unit.
FIG. 2c is a top plan view of a first embodiment of a speaking valve according to the invention in the second position of the valve unit.

FIG. 2 shows the speaking valve 1 of FIG. 1 in a second position of the valve unit 20. FIG. 2a is a side view on to the speaking valve, FIG. 2b is a sectional view along line A-A and FIG. 2c is a plan view from the exterior on to the second end 12 of the tubular housing 13, with the valve unit being completely removed.

In a second position of the valve unit 20 the valve cover 24 is spaced from the second end of the tubular housing 13 so that there is an intermediate space between valve unit and attachment unit. In that position gas exchange is possible through the intermediate space between valve unit 20 or valve cover 24 and attachment unit 10, wherein air can both pass into the attachment unit and also issue therefrom and finally respiration is made possible, as is the case even with a tracheostomy cannula without fitted speaking valve. The action of the valve unit 20 is bypassed in that position of the valve unit 20.

It can be clearly seen from FIG. 2b that, to set the illustrated second position, the valve unit 20 was screwed with its second connecting element 26 out of the first connecting element 14 by half a turn. A further outward screwing movement out of the first connecting element 14 provides further second positions in which the spacing between valve unit 20 and attachment unit 10 is greater than in illustrated FIG. 2. Finally, complete unscrewing is also possible whereby the view shown in FIG. 2c on to the second end 12 becomes visible.

It will be clearly seen from FIG. 2c that the first connecting element 14 extends on the longitudinal axis of the tubular housing 13, and how the tubular housing itself has a rotational symmetry. The connecting element is fixed with four legs 15 to the inside wall of the tubular housing 13. The tubular housing 13, the legs 15 and the first connecting element 14 together form the attachment unit 10.

Figures 3A, 3B:
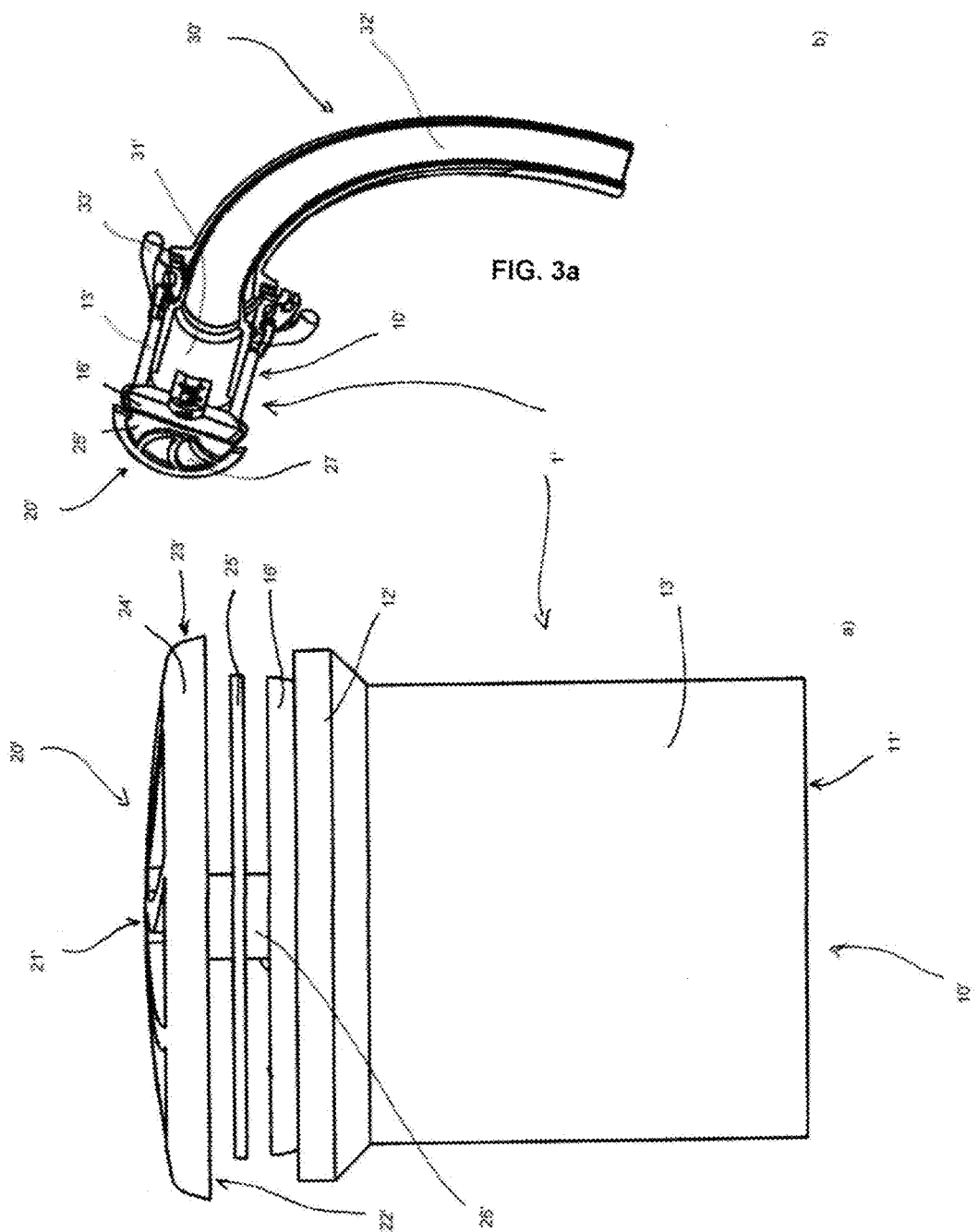
FIG. 3a shows a sectional view of a further embodiment of a speaking valve according to the invention with a tracheostomy cannula.
FIG. 3b shows an elevational view of the further embodiment of FIG. 3a without a tracheostomy cannula.

FIG. 3 shows a further embodiment of a speaking valve 1' according to the invention, wherein FIG. 3a shows a side view on to the speaking valve on a greatly enlarged scale and FIG. 3b shows a perspective view of a longitudinally sectioned tracheostomy cannula with a speaking valve corresponding to the embodiment of FIG. 3a. In both views the valve unit 20' is in a second position relative to the attachment unit 10'. Besides the components already described this speaking valve 1' additionally has a filter element 16' which is arranged within the tubular housing 13' in the region of the second end 12' and projects beyond same.

In this embodiment the filter element 16' is fixed to the second connecting element 26 and moves with same when there is a movement from the first into a second position. The same applies to the valve diaphragm which is fitted at a spacing relative to the filter element on the second connecting element and extends around the second connecting element at the valve cover. The filter element is a disk-shaped material with a central aperture, through which the second connecting element is guided. Replacement of the filter element is possible by completely removing the valve unit from the attachment unit. The filter element comprises a porous plastic and, when the valve unit is in a second position relative to the attachment unit, absorbs moisture from the air exhaled through the speaking valve. Upon subsequent inhalation that is successively delivered to the inhalation air again, thereby providing for moistening of the inhalation air.

FIG. 4 shows a side view of a further embodiment of a speaking valve 1" according to the invention, which is fitted on to a tracheostomy cannula. In this case the valve unit 20" is in a second position relative to the attachment unit 10". In this embodiment the attachment unit 10" is of such a dimension that it converges conically at the inside and the outside from its first end to its second end and the inside wall forms the female element of a 15 mm connector, whereby frictionally locking attachment to a 15 mm connector 31" usually fitted to a tracheostomy cannula is possible. The tracheostomy cannula 30" has a cannula tube 32" with inner and outer cannulae, wherein the inner and outer cannulae are connected together by a union nut. Also disposed on the tracheostomy cannula is a cannula flange plate 33", by means of which fixing to the neck of a patient is made possible while at the same time avoiding pressure points due to the tracheostomy cannula. The speaking valve 1" shown in this view is also of such a configuration that the tubular housing of the attachment element 10" also externally forms a cone and together with the valve unit represents a conical shape corresponding to a male element of a 22 mm connector. That design configuration permits attachment of a respiration tube provided with a female 22 mm connector.

The speaking valve 101 shown in FIGS. 5 through 8 comprises an attachment unit 110 which is in the form of a more or less cylindrical housing 114 having a first end 111 and a second end 112. A central portion of the housing 114 is in the form of connecting elements, insofar as the cylindrical outside of the housing 114 is provided in that region with a male thread 117. The valve unit 120 is in the form of a cap with a valve cover 124 and a cap casing portion 126. The cap casing portion 126 serves at the same time as a connecting element insofar as its inside surface is provided with a female thread 127 which engages matchingly into the male thread of the housing 114. The valve cover 124 of the valve unit has openings 128. In addition, extending inwardly from the valve cover 124 is a holding projection 129 which is arranged centrally at the inside of the valve cover 124 and which holds an elastically movable valve diaphragm fast to the underside of the valve cover for example by means of a threaded sleeve 121.

As can be seen in particular from FIG. 6 the cap-shaped valve unit 126 on its inside at the transition from the cap casing portion 120 to the valve cover 124 has a conical transitional surface which serves as a conical sealing surface 123, wherein the second end 112 of the attachment portion 110 is in the form of a sealing lip 112', by the upper inner edge of the tubular housing 13 being bevelled. When the valve unit 120 has been completely screwed on to the attachment unit 110 the sealing lip 112' is in sealing engagement with the conical sealing surface 123 and thus blocks any transfer from the outside into the inner lumen of the attachment unit 110 by way of the openings 122.

FIGS. 5, 6 and 7 show a position of the valve unit 120 relative to the attachment unit 110, in which the sealing lip 112' partially opens the openings 122 so that air can flow through the openings 122 and the lumen of the attachment unit 110 in both directions, that is to say both for inhalation and also exhalation. Any air which passes through the attachment unit 110 has to pass a filter element 105 which, in the forms of a disk which for example can be between 3 and 5 mm in thickness, covers the entire cross-section of the lumen of the attachment unit 110. The filter or moistening element 105 for example comprises a porous sponge or plastic material and can optionally also be a multi-layer paper material which has a hydrophilic or hygroscopic coating. The flow resistance through the filter element 105 should be as low as possible, but at the same time the filter element should absorb moisture and heat from the exhalation air upon exhalation through the openings 122 of the speaking valve and should at least partially deliver that moisture and heat to the inhaled air. In contrast to the above-described embodiment of FIGS. 1 and 2 the filter element here does not need any aperture and sits, preferably under an elastic radial stressing, in a groove at the inside of the cylindrical housing 114.

In the closed condition as shown for example in FIG. 8 and in which the openings 122 are closed by the sealing lip 112' the speaking valve functions in such a way that, upon inhalation, by virtue of the pressure difference between the environment and the lumen of the attachment unit 110, the valve diaphragm 125 lifts off the sealing leg 119 and as a result the respiratory air can flow through the openings 128 beyond the valve diaphragm 125 and between the gap formed between the sealing leg 119 and the valve diaphragm 125 externally past the valve diaphragm 125 into the lumen of the attachment unit 110.

Upon exhalation the increased pressure within the lumen of the attachment unit 110 causes the valve diaphragm 125 to be pressed against the peripherally extending sealing leg so that access to the openings 128 is blocked and the respiratory air cannot escape by way of the valve but must pass outwardly by way of the natural airways so that in that way the patient has the option to speak. Moreover however it is also possible for the opening gap to the openings 122 to be so adjusted by partially opening the valve, for example into the position shown in FIGS. 5 through 7, that a respective part of the respiratory air flows in and out through the openings 122, but a further part of the air, at any event upon exhalation, also flows by way of the natural airways.

In the upper region the inside wall of the housing 114 has a groove which forms a recess for receiving the edge of the disk-shaped filter element 105 so that the filter element 105 cannot slip in the housing 114.

The valve diaphragm 125 is fixed to a central holding projection 129 extending downwardly from the center of the valve cover 124.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features and emphasis of the independence of the individual features from each other is dispensed here only for the sake of brevity and readability of the description.

The invention is not limited to the disclosed embodiments. Modifications in the disclosed embodiments are apparent to the man skilled in the art from the drawings, the description and the accompanying claims.

REFERENCE NUMERALS 1, 1', 1" speaking valve
10, 10', 10" attachment unit
11, 11', 11" first end
12, 12', 12" second end
13, 13', 13" housing
14, 14', 14" first connecting element
15, 15', 15" legs
16, 16', 16" filter element
20, 20', 20" valve unit
21, 21', 21" outwardly facing side
22, 22', 22" side facing towards the attachment unit
23, 23', 23" peripheral surface
24, 24', 24" valve cover
25, 25', 25" valve diaphragm
26, 26', 26" second connecting element
27, 27', 27" apertures
30, 30', 30" tracheostomy cannula
31, 31', 31" connector
32, 32', 32" cannula tube
33, 33', 33" cannula flange plate

The invention claimed is:

1. A speaking valve for fitment on to a tracheostomy cannula, which includes a valve unit and an attachment unit,
wherein the attachment unit has a tubular housing having a first end and a second end and a longitudinal axis extending from the first end to the second end,
wherein the first end of the attachment unit can be connected to a connector on the tracheostomy cannula and the valve unit is arranged at the second end of the attachment unit and,
wherein the valve unit and the attachment unit are connected together movably,
characterised in that
the valve unit in a first position on said tubular housing closes the tubular housing of the attachment unit airtightly with respect to a flow direction, and
in at least one second position on said tubular housing permits a flow of air into the housing and out of the tubular housing,
wherein the valve unit can be transferred from the first position into the at least one second position by a movement parallel to the direction of the longitudinal axis of the tubular housing,
wherein the valve unit comprises at least one lateral opening in the wall of the valve unit which in the first position is covered by a wall of the attachment unit, that bears against the surroundings of the lateral opening, and in the second position the at least one lateral opening in the wall of the valve unit is opened by the wall of the attachment unit thereby allowing a flow of air through the lateral opening into the tubular housing and out of the tubular housing.

2. The speaking valve as set forth in claim 1 characterised in that the attachment unit has at least one first connecting element and the valve unit has at least one second connecting element, wherein either the first connecting element or the second connecting element has a projection and the respective other connecting element has a receiving opening corresponding thereto, wherein the attachment unit and the valve unit are movably connected together by way of the mutually engaging first and second connecting elements.

3. The speaking valve as set forth in claim 1 characterised in that the at least one projection and the at least one receiving opening are respectively formed by a screwthread or by a latching connection having at least two latching steps or a combination of thread and latching connection.

4. The speaking valve as set forth in claim 1 characterised in that the connecting elements have an inner cylinder and a hollow outer cylinder which engage into each other in concentric and fitting relationship and of which one is respectively fixedly connected to the valve unit and the other to the attachment unit.

5. The speaking valve as set forth in claim 4 characterised in that the cylinder and the hollow cylinder are each of a smaller diameter than the lumen of the tubular attachment unit and are respectively arranged centrally with respect to the attachment unit and the valve unit.

6. The speaking valve as set forth in claim 4 characterised in that the cylinder in turn is a hollow cylinder and the cylinder and the hollow cylinder are formed by the tubular housing of the attachment unit and a cylindrical casing portion of a cap-shaped valve unit.

7. The speaking valve as set forth in claim 1 characterised in that an air-permeable filter element is arranged in the flow cross-section of the second end of the tubular housing of the attachment unit.

8. The speaking valve as set forth in claim 7 characterised in that the filter element has a material for storing heat and/or moisture.

9. The speaking valve as set forth in claim 1 characterised in that the valve unit has a disk-shaped apertured valve cover and an elastic valve diaphragm which can be applied sealingly on the inside of the valve cover and which covers over the apertures and lifts off a valve seat at the inside of the valve cover at least when a predeterminable pressure difference between the outside and the inside of the valve unit is exceeded.

10. The speaking valve as set forth in claim 9 characterised in that the valve diaphragm has edge regions and a central region, wherein the central region is fixed to the valve cover in such a way that the edge regions of the diaphragm can lift elastically off the valve seat in the direction of the attachment unit under the action of a corresponding pressure force.

11. The speaking valve as set forth in claim 9 characterised in that the valve cover is also formed from an elastic material and in the first position bears with a prestressing against the second end of the housing and in the second position opens a passage gap relative to the upper edge of the second end of the tubular housing of the attachment unit.

12. The speaking valve as set forth in claim 1 characterised in that the valve unit is in the form of a valve cap having a cylindrical cap casing portion and a disk-shaped valve cover.

13. The speaking valve as set forth in claim 12 characterised in that the cap casing portion embraces at least the second end of the tubular housing from the outside, wherein a sealing surface is provided on the inside of the valve cover or at the transition between the cap casing portion and the valve cover, which sealing surface in the first position is in sealing engagement with the upper edge of the second end of the tubular housing.

14. The speaking valve as set forth in claim 1 characterised in that the upper edge of the second end of the tubular housing is in the form of a sealing lip.

15. The speaking valve as set forth in claim 1 characterised in that the peripheral surface of the valve unit has a grooving, a roughening in the peripheral surface.

16. The speaking valve as set forth in claim 1 characterised in that the valve unit has one or more markings on its outwardly facing side.

17. The speaking valve as set forth in claim 1 characterised in that provided between the valve unit and the attachment unit for at least one of the first and second positions are latching elements which audibly latch together.

18. The speaking valve as set forth in claim 1 wherein the housing of the attachment unit and the peripheral surface of the valve unit are together of a conically outwardly tapering shape.

19. The speaking valve as set forth in claim 1 characterised in that the first end of the attachment unit can be fitted on to the connector in frictionally locking relationship.

20. The speaking valve as set forth in claim 1 wherein in the second position there is a ring-shaped passage of about 2 to 5 mm in height in the direction of the longitudinal axis of the tubular housing between an edge of the tubular housing and the valve unit thereby allowing a flow of air through the ring-shaped passage into the tubular housing and out of the tubular housing.

21. The tracheostomy cannula having a speaking valve as set forth in claim 1.

22. A speaking valve for fitment on to a tracheostomy cannula, which includes a valve unit and an attachment unit,
   wherein the attachment unit has a tubular housing having a first end and a second end and a longitudinal axis extending from the first end to the second end,
   wherein the first end of the attachment unit can be connected to a connector on the tracheostomy cannula and the valve unit is arranged at the second end of the attachment unit and,
   wherein the valve unit and the attachment unit are connected together movably,
   characterised in that
   the valve unit in a first position on said tubular housing closes the tubular housing of the attachment unit airtightly with respect to a flow direction, and
   in at least one second position on said tubular housing permits a flow of air into the housing and out of the tubular housing,
   wherein the valve unit can be transferred from the first position into the at least one second position by a movement parallel to the direction of the longitudinal axis of the tubular housing,
   wherein in the second position there is a ring-shaped passage of about 2 to 5 mm in height in the direction of the longitudinal axis of the tubular housing between an edge of the tubular housing and the valve unit thereby allowing a flow of air through the ring-shaped passage into the tubular housing and out of the tubular housing.

* * * * *